United States Patent
Iseki et al.

(10) Patent No.: US 8,436,323 B2
(45) Date of Patent: May 7, 2013

(54) PARTICLE BEAM IRRADIATION APPARATUS AND PARTICLE BEAM IRRADIATION METHOD

(75) Inventors: Yasushi Iseki, Yokohama (JP); Katsushi Hanawa, Kita-Ku (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 260 days.

(21) Appl. No.: 12/677,677

(22) PCT Filed: Sep. 12, 2008

(86) PCT No.: PCT/JP2008/066542
§ 371 (c)(1),
(2), (4) Date: Mar. 11, 2010

(87) PCT Pub. No.: WO2009/035080
PCT Pub. Date: Mar. 19, 2009

(65) Prior Publication Data
US 2010/0187435 A1    Jul. 29, 2010

(30) Foreign Application Priority Data
Sep. 12, 2007   (JP) .................................. 2007-236399

(51) Int. Cl.
*A61N 5/10*    (2006.01)
(52) U.S. Cl.
USPC ......................................... 250/492.1; 378/65
(58) Field of Classification Search .................. 250/398, 250/492.3, 492.1; 378/65
See application file for complete search history.

(56) References Cited

U.S. PATENT DOCUMENTS

| | | | | |
|---|---|---|---|---|
| 4,726,046 | A * | 2/1988 | Nunan | 378/65 |
| 6,717,162 | B1* | 4/2004 | Jongen | 250/505.1 |
| 7,554,275 | B2 * | 6/2009 | Amaldi | 315/505 |
| 2006/0231775 | A1* | 10/2006 | Harada | 250/492.3 |
| 2010/0176309 | A1* | 7/2010 | Mackie et al. | 250/492.3 |
| 2010/0317968 | A1* | 12/2010 | Wright et al. | 600/427 |
| 2011/0186755 | A1* | 8/2011 | Otto | 250/492.3 |
| 2012/0305790 | A1* | 12/2012 | Hanawa et al. | 250/393 |

FOREIGN PATENT DOCUMENTS

| | | |
|---|---|---|
| JP | 11 319123 | 11/1999 |
| JP | 2005 74156 | 3/2005 |
| JP | 2005 111151 | 4/2005 |
| JP | 2008 154627 | 7/2008 |
| JP | 2008-154627 A | 7/2008 |

OTHER PUBLICATIONS

Japanese Office Action issued Sep. 11, 2012 in Patent Application No. 2009-532240.

* cited by examiner

*Primary Examiner* — David A Vanore
*Assistant Examiner* — Wyatt Stoffa
(74) *Attorney, Agent, or Firm* — Oblon, Spivak, McClelland, Maier & Neustadt, L.L.P.

(57) ABSTRACT

A particle beam irradiation apparatus includes: a beam generation unit that generates a particle beam; a beam emission control unit that controls emission of the particle beam; a beam scanning instruction unit that sequentially two-dimensionally instructs a position of the particle beam so that the particle beam is scanned across the entire slice; a beam scanning unit that two-dimensionally scans the particle beam; a respiration gate generation unit that generates a respiration gate synchronized with a respiration cycle of the patient; and a pulse generation unit that generates a predetermined number of scanning start pulses at substantially equally spaced time intervals in the respiration gate. The beam scanning instruction unit instructs to scan the entire slice by pattern irradiation based on a set dose from each of the scanning start pulses so that a scan of the same slice is repeated the predetermined number of times.

15 Claims, 13 Drawing Sheets

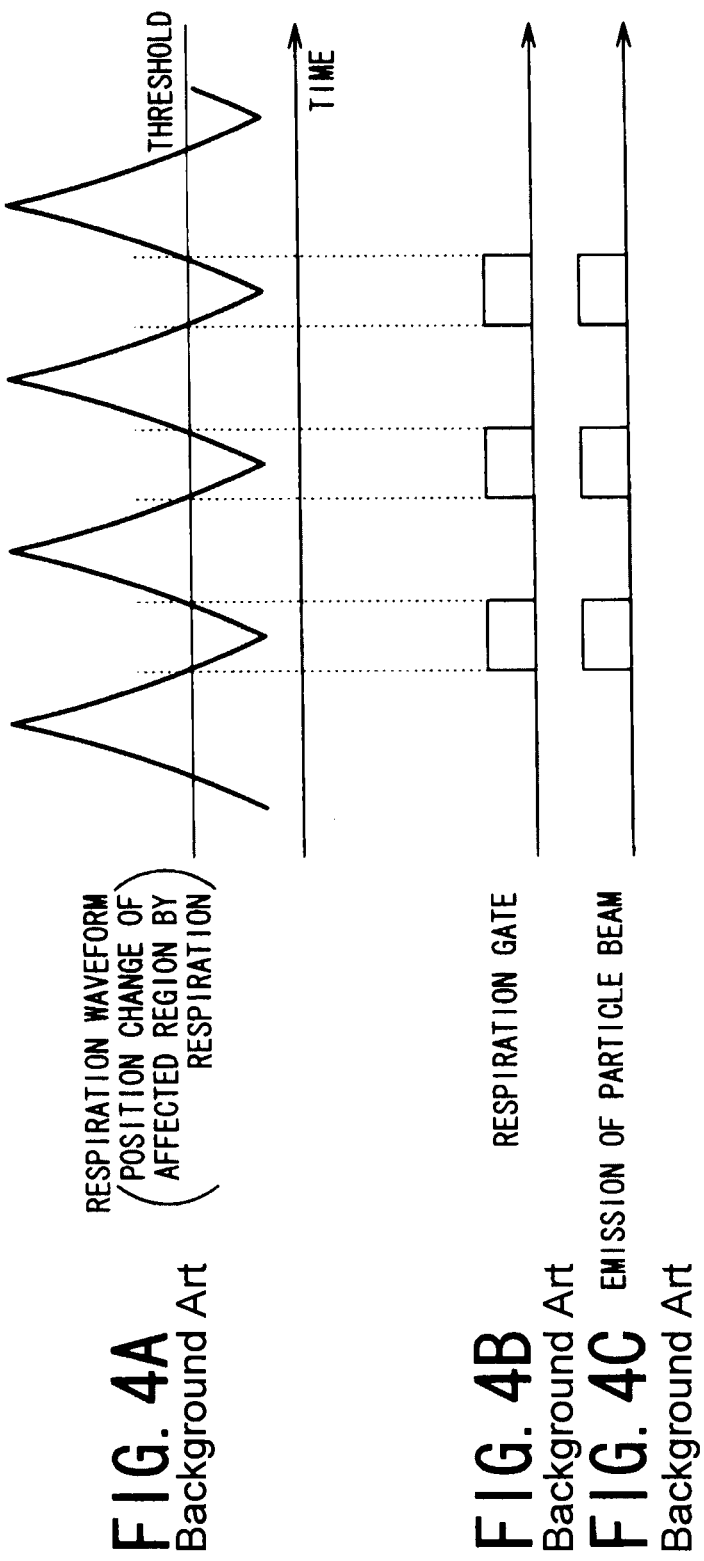

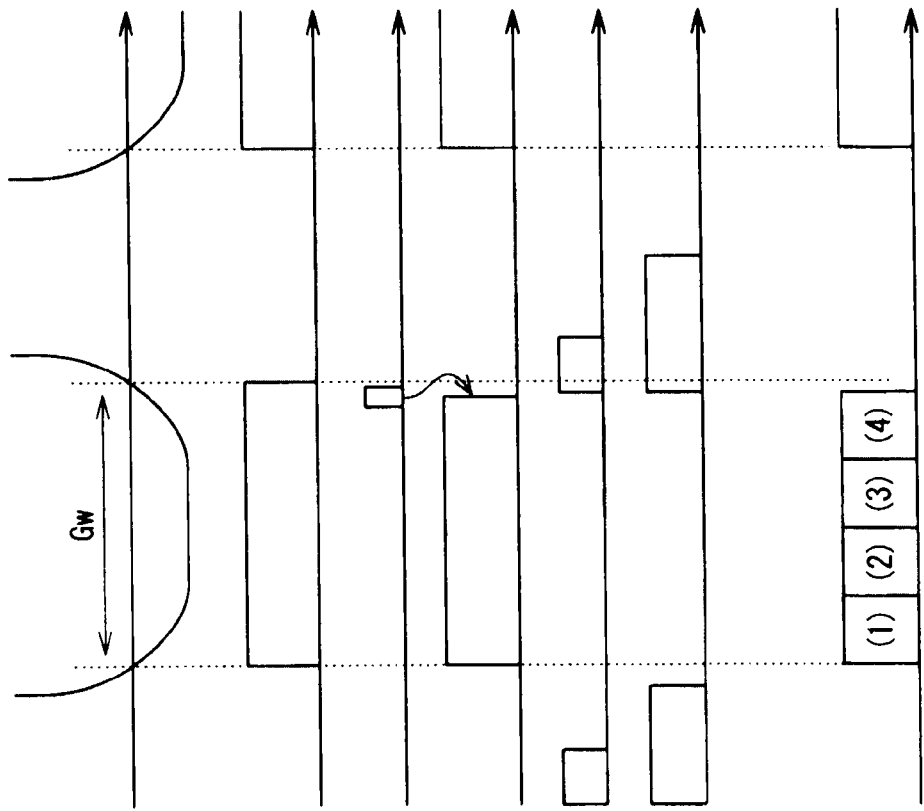

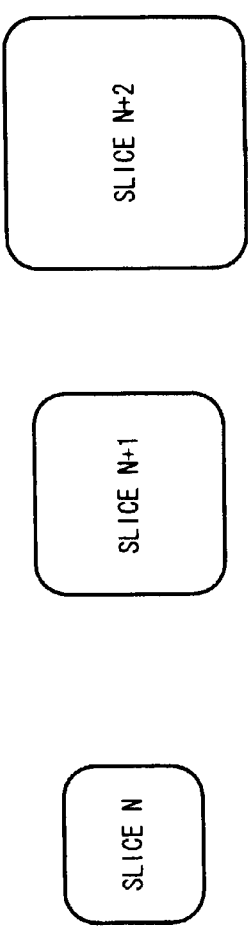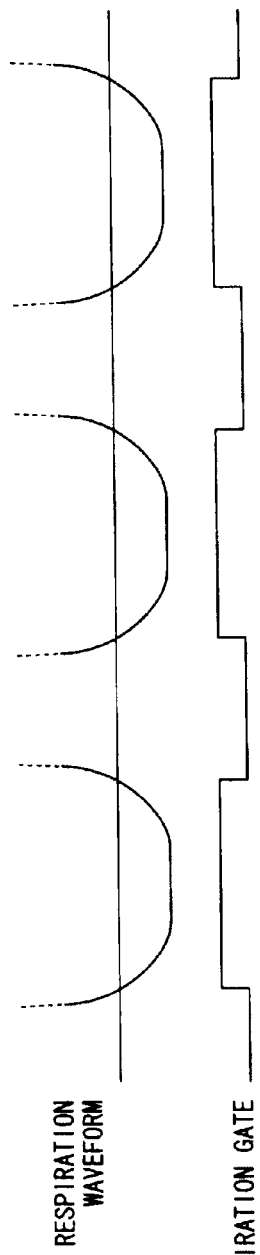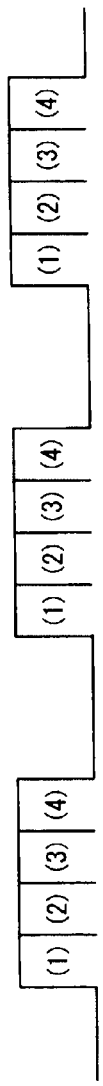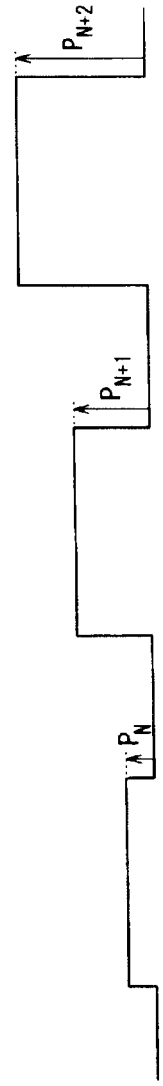
FIG. 6A Background Art    SLICE
FIG. 6B Background Art    RESPIRATION WAVEFORM
FIG. 6C Background Art    RESPIRATION GATE
FIG. 6D Background Art    REPEATED SCANS (FOUR TIMES)
FIG. 6E Background Art    BEAM INTENSITY

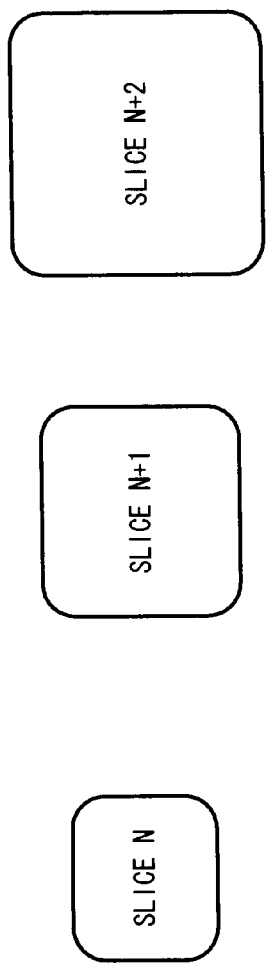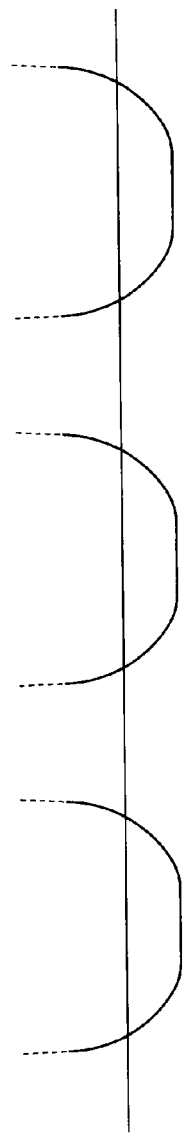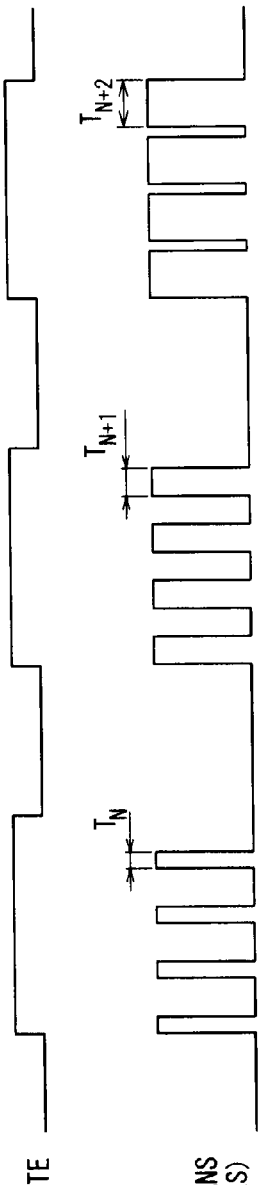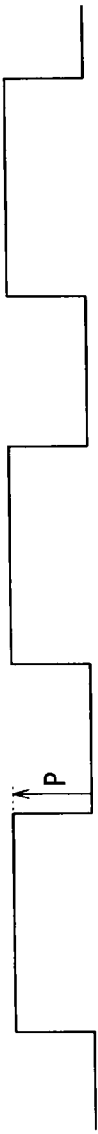
FIG. 8A SLICE
FIG. 8B RESPIRATION WAVEFORM
FIG. 8C RESPIRATION GATE
FIG. 8D REPEATED SCANS (FOUR TIMES)
FIG. 8E BEAM INTENSITY

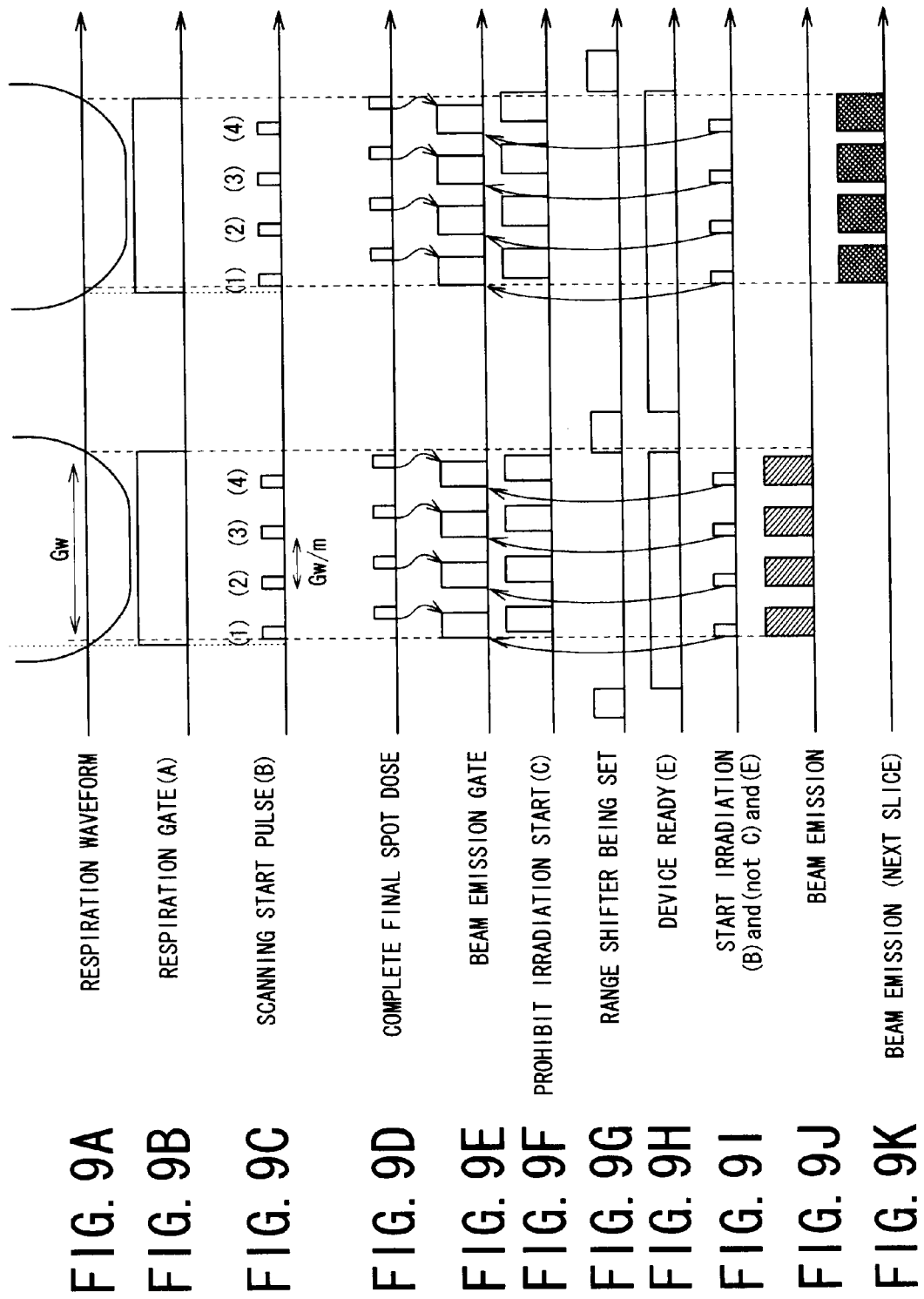

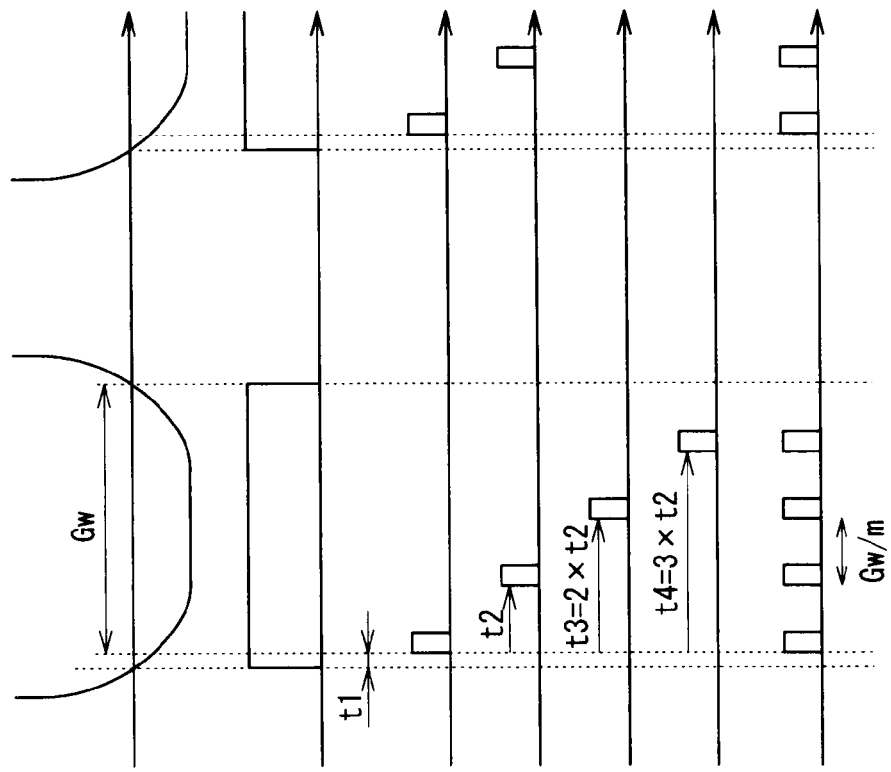

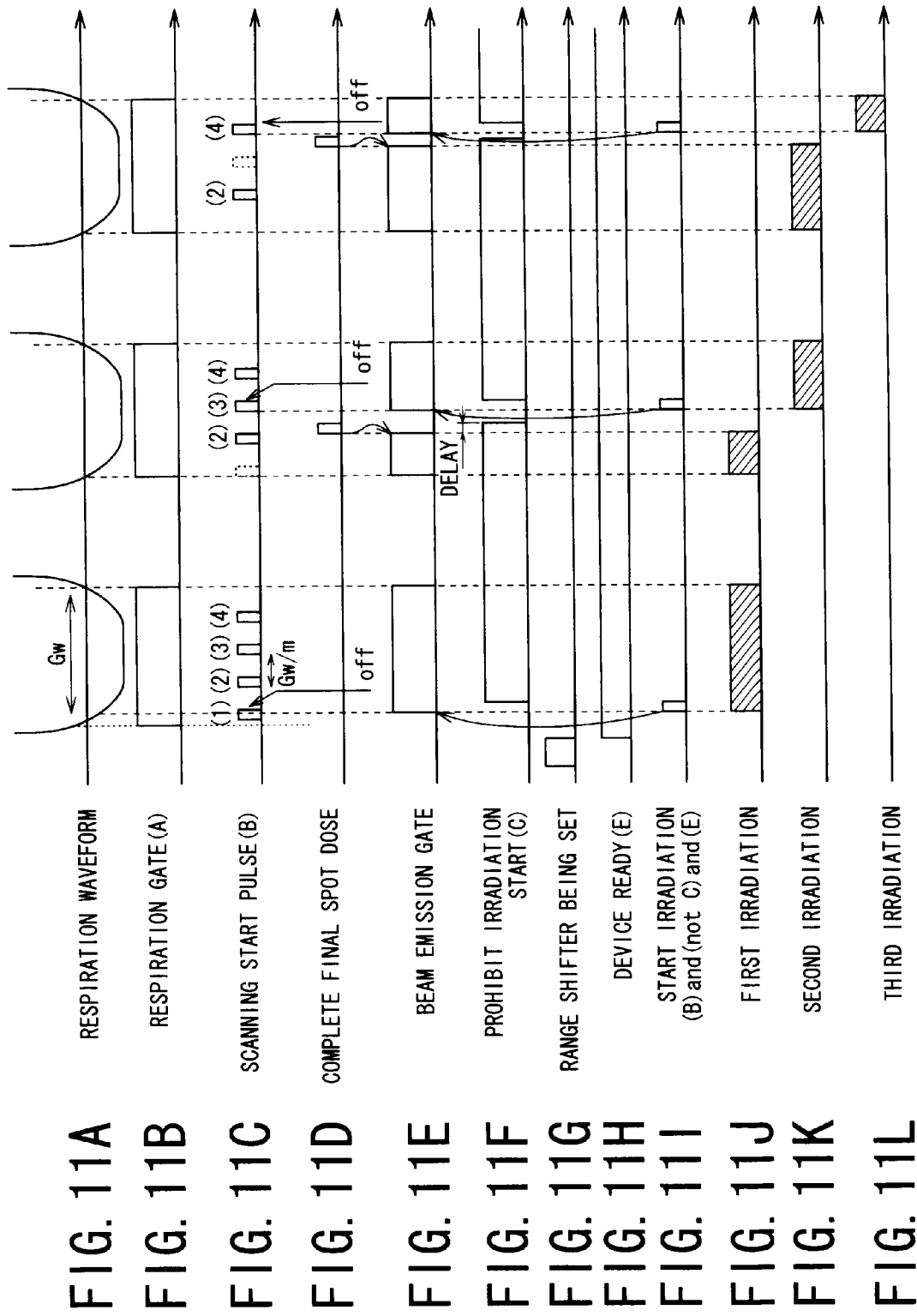

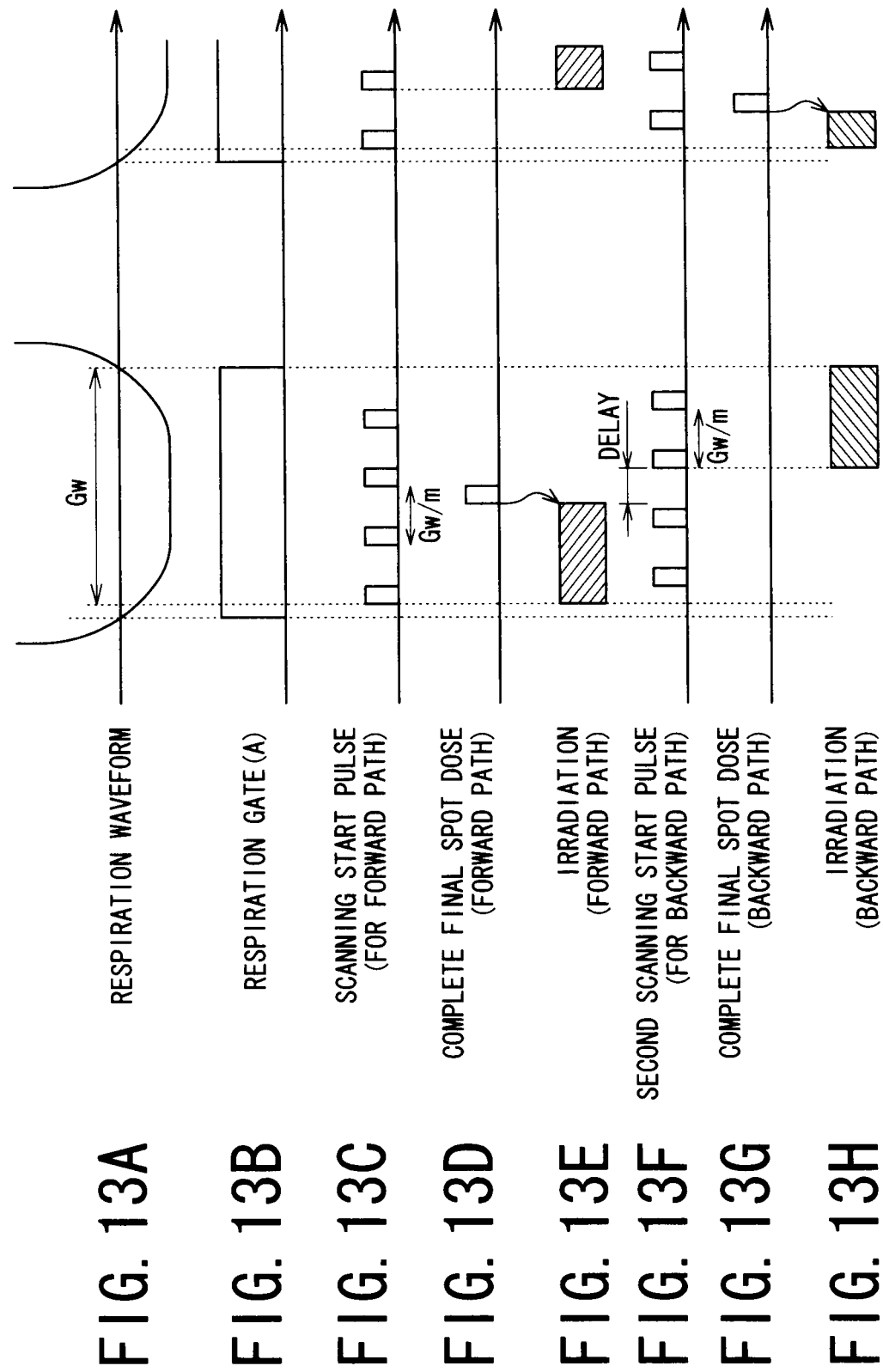

PARTICLE BEAM IRRADIATION APPARATUS AND PARTICLE BEAM IRRADIATION METHOD

TECHNICAL FIELD

The present invention relates to a particle beam irradiation apparatus and a particle beam irradiation method, and more particularly to a particle beam irradiation apparatus and a particle beam irradiation method for irradiating an affected region of the body with a heavy particle beam such as a carbon beam, or a proton beam for cancer therapy.

BACKGROUND ART

Cancer is now the leading cause of death in Japan, and more than 300 thousand people die of cancer every year. Under such circumstances, a particle beam therapy method using a heavy particle beam such as a carbon beam, a proton beam has been attracting attention because of its superior features such as a high therapy effect, fewer side effects, or less physical burden. With this therapy method, a particle beam emitted from an accelerator is applied to cancer cells to kill the cancer cells with a little influence on normal tissues.

A currently used particle beam irradiation method in this therapy method is referred to as an expanded beam method. In the expanded beam method, a beam diameter of a particle beam is expanded to the size of an affected region or more by a method referred to as a wobbler method or a double scatterer method. Then, a brass collimator referred to as a shape collimator is used to limit an irradiation region to substantially match a beam shape with the shape of the affected region. In a beam traveling direction (beam axis direction), the beam is expanded by a beam range expansion device referred to as a ridge filter, and a beam range shaping device made of polyethylene referred to as a bolus matches a beam stop position with the shape (outline) of the affected region in a deep position for irradiation.

However, the expanded beam method cannot strictly three-dimensionally match the beam with the shape of the affected region, and there is a limit in reducing influence on normal tissues around the affected region. In addition, the shape collimator and the bolus are produced for each affected region (and further, each irradiation direction of the affected region), and thus remain as radiation waste after therapy irradiation.

Then, as a further advanced irradiation method of particle beam therapy, a three-dimensional irradiation method of three-dimensionally irradiating an in-body affected region to target cancer cells with higher accuracy has been developed (see Patent Document 1: Japanese Patent Laid-Open No. 2001-212253; Non-patent Document 2: Yasuyuki Futami, and eight others; "Broad-beam three-dimensional irradiation system for heavy-ion radiotherapy at HIMAC"; Nuclear Instruments and Methods in Physics Research A 430 (1999) 143-153; 19, Jan. 1999, or the like).

One of three-dimensional irradiation methods is a method referred to as a scanning irradiation method. This method virtually divides a therapy area into a three-dimensional lattice points and performs irradiation of each lattice point. With such a three-dimensional irradiation method, a beam can be matched with an affected region also in a beam axis direction with high accuracy without using a shape collimator or a bolus, and exposure of normal tissues can be prevented as compared with a conventional two-dimensional irradiation method.

However, the scanning irradiation method has a problem described below. Conventionally, in particle beam therapy, for an organ whose area is moved with respiration such as lung or liver, a respiration waveform signal is obtained, and in-gate irradiation is performed that is irradiation performed only when the area is within a certain position range. However, in the scanning irradiation method, irradiation points are sequentially switched to cause relative displacement of the irradiation points with the movement of the area by respiration, causing non-uniform dose distribution in an irradiation region. To solve this problem, Non-patent Document 1 proposes a respiration synchronized irradiation method described below. In this method, one irradiation time (a time for one irradiation of the entire irradiation region in a slice to be irradiated) in one slice (a planar divided unit of an affected region divided in a beam axis direction) is set to be 1/m of a gate width of one respiration. Then, scanning irradiation of the same slice is repeated m times (for example, m=eight times) in one respiration. After the m time scanning irradiation of the target slice is finished, a slice to be irradiated is changed, and m time scanning irradiation of a next slice to be irradiated is performed in the same manner. In this method, the gate width of the one respiration is divided into m parts, scanning start times for the same slice are dispersed in the gate width of the one respiration (referred to as phase control in Non-patent Document 1), and irradiation of the same slice is repeated m times (referred to as rescanning in Non-patent Document 1. Non-patent Document 1: Takuji Furukawa, and eight others, "Design review of three-dimensional scanning irradiation apparatus", HIMAC report of National Institute of Radiological Sciences: HIMAC-124, issued by Independent administrative institute, National Institute of Radiological Sciences, April, 2007). As a result, even if the irradiation region is moved in the gate width of one respiration, changes in dose for the irradiation region due to the movement can be reduced by an integral effect, and dose uniformity can be improved according to a statistical error of $1/\sqrt{m}$.

However, the phase control rescanning irradiation proposed in Non-patent Document 1 has a problem described below. Generally, the size of an affected region of a patient is not uniform in a beam axis direction. Specifically, each slice has a different area, and each slice has a different number of lattice points.

In contrast, the gate width of one respiration does not significantly change though there are some changes. However, a scanning time for one of the m divided parts of the gate width of one respiration needs to be the same for every slice as long as the number m for one slice is fixed. This implies that an irradiation time for one lattice point is reduced for a slice with many lattice points (slice with a large area), while an irradiation time for one lattice point is increased for a slice with a few lattice points (slice with a small area).

On the other hand, the dose is determined by a product of an irradiation time and beam intensity. Thus, for example, when the same dose is required for each slice in therapy planning, high beam intensity needs to be set for the slice with many lattice points (slice with a large area), while low beam intensity needs to be set for the slice with a few lattice points (slice with a small area). Specifically, the beam intensity needs to be changed for each slice in the phase control rescanning irradiation proposed in Non-patent Document 1. Also, to achieve the dose determined by therapy planning with high accuracy, the beam intensity needs to be adjusted with high accuracy.

However, the beam intensity is adjusted by control of an upstream device such as an accelerator. It takes time to adjust the beam intensity, and once the beam intensity is changed, it is difficult to ensure reproducibility of beam properties (actual beam intensity, beam position, or beam size) when the beam is introduced into the irradiation apparatus. It can be supposed that the beam properties are checked and the result is adjusted by control of the upstream device, but this is not realistic because of an increased therapy time.

In the phase control rescanning irradiation, the respiration waveform signal of the patient is previously obtained, and the gate width of one respiration is set based on an amplitude and a cycle of the previously obtained respiration waveform. Then, based on the set gate width, proper beam intensity is calculated for each slice to design an irradiation pattern (therapy planning). If, therefore, the previously obtained respiration waveform does not match a respiration waveform when the patient lies down on a therapy bed in therapy irradiation, uniformity of dose distribution may be lost in one planned slice surface. Particularly, in actual therapy, the respiration waveform may change during therapy irradiation, and therefore non-uniformity of dose distribution in such a case may become a serious problem.

(Configuration and Operation of Conventional Apparatus)

In view of the above-described points, a specific configuration and operation of a conventional apparatus will be described.

FIG. 1 shows an exemplary configuration of a conventional particle beam irradiation apparatus 300 using a respiration synchronized irradiation method. The particle beam irradiation apparatus 300 includes a beam generation unit 10, a beam emission control unit 20, a beam scanning unit 30, a beam scanning instruction unit 40, a dose monitor unit 50, a position monitor unit 51, a ridge filter 60, a range shifter 70, a control unit 80, a respiration measurement unit 81, a respiration gate generation unit 82, or the like.

The particle beam irradiation apparatus 300 is an apparatus that irradiates an affected region 200 of a cancer patient 100 with a particle beam obtained by accelerating particles of carbon or the like or protons to high speeds for cancer therapy. The particle beam irradiation apparatus 300 can discretize the affected region 200 into three-dimensional lattice points, and perform a three-dimensional scanning irradiation method of sequentially scanning the lattice points with a particle beam with a small diameter.

Specifically, the affected region 200 is divided in a particle beam axis direction (a Z-axis direction in a coordinate system on the upper right in FIG. 1) by flat plate units referred to as slices, two-dimensional lattice points (lattice points in X-axis and Y-axis directions in a coordinate system on the upper right in FIG. 1) of divided slices such as a slice N, a slice N+1, and a slice N+2 are sequentially scanned for three-dimensional scanning.

The beam generation unit 10 generates particles of carbon ions or protons, and an accelerator such as a synchrotron accelerates the particles to such energy that can reach deep into the affected region 200 to generate a particle beam 90.

The beam emission control unit 20 performs on/off control of emission of the generated particle beam 90 based on a control signal output from the control unit 80.

The beam scanning unit 30 deflects the particle beam 90 in an X direction and a Y direction and two-dimensionally scans a slice surface, and includes an X electromagnet 30a for scanning in the X direction and a Y electromagnet 30b for scanning in the Y direction. To the X electromagnet 30a and the Y electromagnet 30b, a driving current of each electromagnet is applied from the beam scanning instruction unit 40 as an instruction signal to instruct a scanning position.

The range shifter 70 controls a position in the Z-axis direction of the affected region 200. The range shifter 70 is constituted by, for example, acrylic plates having different thicknesses. By combining the acrylic plates, energy of the particle beam passing through the range shifter 70 can be gradually changed. That is, an in-body range can be changed depending on the position in the Z-axis direction of the slice of the affected region 200. The in-body range by the range shifter 70 is generally controlled to be changed at regular space intervals, and the interval corresponds to an interval between lattice points in the Z-axis direction. The in-body range may be switched, as mentioned above, by inserting an object for attenuation such as the range shifter 70 on a path of the particle beam, or instead, may be switched by changing energy itself of the particle beam by controlling the upstream device.

The ridge filter 60 is provided to diffuse sharp peaks referred to as Bragg peaks of the dose in an in-body depth direction. A diffusion width of the Bragg peak by the ridge filter 60 is set to be equal to the thickness of the slice, that is, the interval between the lattice points in the Z-axis direction. The ridge filter 60 for three-dimensional scanning irradiation is constituted by a plurality of aluminum rod members each having a substantially isosceles triangular section. A difference in path length caused when the particle beam passes through the isosceles triangle allows the Bragg peaks to be diffused, and the shape of the isosceles triangle allows the diffusion width to be set to a desired value.

The dose monitor unit 50 monitors the dose of irradiation, and includes, in a casing thereof, an ionization chamber that collects charges generated by an ionization effect of the particle beam with a parallel electrode, a SEM (Secondary Electron Monitor) device that measures secondary electrons emitted from a secondary electron emission film placed in the casing, or the like.

The position monitor unit 51 identifies whether the particle beam scanned by the beam scanning unit 30 is located in a proper position, includes a configuration similar to that of the dose monitor unit 50, and uses a charge collecting electrode that is, for example, divided into strips or includes a plurality of wires.

The control unit 80 controls the entire particle beam irradiation apparatus 1, performs on/off control of beam emission to the beam emission control unit 20, sends instructions on beam scanning to the beam scanning instruction unit 40, and performs control of a range shift amount with slice changes of the range shifter 70, and so on.

The beam scanning instruction unit 40 determines scanning positions in the X direction and the Y direction or scanning timing of each slice based on the instructions from the control unit 80, and outputs a driving current of the X electromagnet 30a or the Y electromagnet 30b to the beam scanning unit 30.

The respiration measurement unit 81 and the respiration gate generation unit 82 are both used for operation using a respiration synchronized irradiation method, and functions thereof will be described later.

FIG. 2 is a flowchart showing an example of a basic process (process without respiration synchronization) of three-dimensional scanning irradiation by the conventional apparatus.

First, an affected region is virtually divided into a plurality of slices along a beam axis, and one of the divided slices is selected. For example, a slice in the deepest position in the affected region is first selected. Also, incident energy of a particle beam and a combination of acrylic plates in the range shifter 70 are selected and set depending on the position of the selected slice (Step ST1).

Then, the number M of lattice points to be irradiated with the particle beam and a lattice point position $(X_i, Y_i)$ [i=1 to M] that is a spot to be irradiated are selected depending on the shape of the affected region in the deepest slice, and the beam scanning unit 30 sets a direction of the particle beam to the lattice point position (Xi, Yi) on the slice (Step ST2). Then, emission of the particle beam is started (Step ST3). Energy distribution of the particle beam output from the beam scanning unit 30 is expanded in the Z-axis direction by the ridge filter 60 so that an in-body range distribution width corresponds to the slice width.

The irradiation dose for the lattice point (Xi, Yi) is monitored by the dose monitor 4, and when the irradiation dose for the target lattice point reaches a planned dose, a dose completion signal is output to the control unit 80, and the control unit 80 receives the signal (Step ST4).

The three-dimensional scanning irradiation method is mainly classified into a spot scanning method and a raster scanning method. The spot scanning method is a method of stopping beam emission while the position of the particle beam is moved from a certain lattice point to a next lattice point, and restarting the beam emission after the completion of the movement. Thus, the beam emission is intermittently performed during a scan of the same slice.

On the other hand, the raster scanning method is a method of continuing beam emission without stopping even while the position of the particle beam is moved from a certain lattice point to a next lattice point. Specifically, the beam emission is continuously performed during a scan of the same slice.

In both the spot scanning method and the raster scanning method, the position of the particle beam is kept at a lattice point until a planned dose at each lattice point is reached, and moved to a next lattice point after the planned dose is reached.

In Step ST5, it is determined which of the spot scanning method and the raster scanning method is used. When the spot scanning method is used, the beam emission is once stopped (Step ST6), and the beam position is moved to a next spot. This process is repeated to a final spot of the target slice (Step ST7).

Meanwhile, when the spot scanning method is not used, that is, when the raster scanning method is used, the beam emission is continued to the final spot without stopping the beam emission.

When irradiation of one slice is finished (YES in Step ST7), the beam emission is once stopped in both the spot scanning method and the raster scanning method, the process returns to Step ST1, and a next slice is selected and setting of the range shifter 70 is changed. The above-described processes are repeated until a final slice is reached (Step ST9).

Specifications required for the above-described irradiation procedure are described, for example, in a data file referred to as an irradiation pattern file, and the data file is transferred to the control unit 80 before start of therapy irradiation. In the irradiation pattern file, a range shifter thickness that provides a slice position, a driving current value of the X electromagnet 30*a* and the Y electromagnet 30*b* that provide a beam position corresponding to the lattice point (X, Y), an irradiation dose for each lattice point, or the like are described for each lattice point in order of irradiation.

FIG. 3 shows an example of a conventional scanning pattern on a slice. A path pattern from a start lattice point A to a final lattice point B is previously determined by therapy planning, and a particle beam is sequentially scanned in one direction along the path pattern.

Next, a conventionally proposed respiration synchronized irradiation method will be described. In the case that an affected region 200 is in an organ such as lung or liver that is treated by the respiration synchronized irradiation method, for example, an LED (not shown) or the like is attached to chest of the patient (not shown in FIG. 1). An image of a movement of the LED is obtained by a respiration measurement unit 81 constituted by a video camera or the like, and the movement of the LED is further made into one-dimensional data to obtain a respiration waveform signal. The respiration waveform signal is sent to the respiration gate generation unit 82, and a respiration gate is generated only during a period when the respiration waveform is lower than a predetermined threshold. The respiration gate is sent to the beam emission control unit 20, the beam is emitted only during a period when the respiration gate is on, and the beam emission is stopped during a period when the respiration gate is off.

FIGS. 4A to 4C show a relationship between a respiration waveform signal (signal corresponding to a position change of an affected region by respiration), a threshold, a respiration gate, and beam emission. For spot scanning irradiation, beam emission and beam stop are further switched in movement of the spot position (this time interval is much shorter than a respiration synchronized gate signal), which is herein omitted (hereinafter the same).

Next, the respiration synchronized irradiation method (phase control rescanning irradiation method) in three-dimensional scanning irradiation proposed in Non-patent Document 1 will be described with reference to timing charts in FIGS. 5A to 5G. In this irradiation method, irradiation in one slice surface is repeated m times for one respiration gate to perform irradiation. In this case, beam intensity is adjusted so that m time irradiation in the slice surface just matches a time of one respiration gate width Gw. FIGS. 5A to 5G illustrate a case where four (m=4) time repeated irradiation is performed for one respiration gate.

First, a combination of acrylic plates of the range shifter 70 is set so that a beam range matches a next slice position. Simultaneously, the beam generation unit 10 constituted by an accelerator or the like adjusts the beam intensity. When the beam emission control unit 20 receives a setting completion signal of the range shifter 70 from the control unit 80, and receives a beam intensity setting completion signal from the beam generation unit 10, the beam emission control unit 20 enters a beam emission ready state. Then, beam emission starts in synchronism with a start of a respiration gate and beam emission. Thereafter, the beam scanning unit 30 performs beam scanning every time a dose completion signal from the dose monitor 50 is received, and irradiation and scanning of the lattice points in the slice surface are sequentially performed. In the spot scanning method, the beam emission is stopped when the particle beam is moved from a certain lattice point to a next lattice point, while in the raster scanning method, the beam emission is not stopped even during movement between the lattice points. Irradiation is performed up to a final lattice point and then a first scan for the slice is finished. This is automatically repeated m times for the slice, and when m time irradiation for all the lattice points is finished, the control unit 80 sends a one slice surface irradiation completion signal to the beam emission control unit 20 to stop the beam emission. Timing for providing the one slice surface irradiation completion signal is set a short time before the respiration gate is closed (see FIGS. 5B, 5C and 5D).

Then, the range shifter 70 is reset so that the beam range matches a next slice position. Simultaneously, beam intensity of the beam generation unit 10 is readjusted. When the beam emission control unit 20 receives a setting completion signal of the range shifter 70 from the control unit 80, and receives a beam intensity setting completion signal from the beam generation unit 10, the beam emission control unit 20 reenters the beam emission ready state, and starts a next respiration gate and starts beam emission for a new slice.

In this irradiation method, beam intensity for each slice is determined as described below. First, a respiration waveform of a patient is previously obtained, and a respiration gate width Gw is calculated from the waveform and a threshold. Then, beam intensity for each slice is determined so that a total time when m repeated scans are performed in each slice surface substantially matches the respiration gate width Gw. This is determined in the stage of therapy planning.

As described above, generally, the size of an affected region of a patient is not uniform in a beam axis direction. Specifically, as shown in FIGS. 6A to 6E, each slice has a different area, and the number of lattice points in the slice increases with increasing area of the slice. Meanwhile, the gate width of one respiration does not significantly change though there are some changes. Thus, a scanning time for one slice of the m divided parts of the gate width of one respiration needs to be the same for every slice (see FIG. 6D). This means that an irradiation time for one lattice point is reduced for a slice with many lattice points (slice with a large area) like the slice N+2 shown in FIG. 6A, while an irradiation time for one lattice point is increased for a slice with a few lattice points (slice with a small area) like the slice N.

On the other hand, the dose for each slice is determined by a product of an irradiation time and beam intensity at the lattice points in the slice. Thus, for example, when the same dose is required for each slice in therapy planning, high beam intensity needs to be set for the slice with many lattice points (slice with a large area), while low beam intensity needs to be set for the slice with a few lattice points (slice with a small area) (see FIG. 6E). Specifically, the beam intensity needs to be changed for each slice in the phase control rescanning irradiation proposed in Non-patent Document 1. Thus, the respiration synchronized irradiation method proposed by the Non-patent Document 1 has problems described below.

First, the beam generation unit 10 needs to adjust beam intensity for each slice. When a beam intensity determined before start of therapy is newly set to the apparatus, beam properties such as actual beam intensity, beam position (axial deviation), or beam size are checked in a usual procedure. However, checking these beam properties every time the beam intensity is changed extremely increases a therapy time, which is unrealistic. Thus, therapy irradiation with insufficient check of the beam properties may be performed. This prevents uniformity of dose distribution on the slice surface from being ensured.

Also, since the respiration gate width is set based on the previously obtained respiration waveform, and the beam intensity is determined based on the set respiration gate width, uniform dose distribution cannot be obtained when the respiration waveform does not match the respiration waveform of the patient immediately before start of the therapy and when the respiration waveform changes during the therapy.

Further, therapy planning is performed using the beam intensity as a parameter, which may provide a complicated calculation method of the therapy planning. Complicated therapy planning prevents an optimum solution from being obtained.

Also, the beam intensity needs to be adjusted, which requires, for example, a large dynamic range of the dose monitor 50 or the like and increases costs. Particularly, for a slice with a short irradiation time, irradiation is performed with reduced beam intensity, which may reduce the S/N ratio of the monitor.

DISCLOSURE OF THE INVENTION

The present invention is achieved in view of the above-described circumstances, and has an object to provide a particle beam irradiation apparatus and a particle beam irradiation method using a respiration synchronized irradiation method to eliminate the need for changing beam intensity for each slice to achieve high dose setting accuracy and a reduced therapy time, and can achieve high uniformity of dose distribution even if a respiration waveform changes during therapy irradiation.

To achieve the above-described object, a particle beam irradiation apparatus according to the present invention includes: a beam generation unit that generates a particle beam; a beam emission control unit that controls emission of the particle beam; a beam scanning instruction unit that sequentially two-dimensionally instructs a position of the particle beam so that the particle beam is scanned across the entire slice, the slice being obtained by dividing an affected region to be irradiated in an axis direction of the particle beam; a beam scanning unit that two-dimensionally scans the particle beam based on an instruction signal from the beam scanning instruction unit; a respiration measurement unit that obtains an amount of movement of the affected region of a patient or a respiration waveform of a patient; a respiration gate generation unit that generates a respiration gate synchronized with a respiration cycle of the patient based on a signal output from the respiration measurement unit; and a pulse generation unit that generates a predetermined number of scanning start pulses at substantially equally spaced time intervals in the respiration gate, wherein the beam scanning instruction unit instructs to scan the entire slice by pattern irradiation based on a set dose from each of the scanning start pulses so that a scan of the same slice is repeated the predetermined number of times, the beam emission control unit permits emission of the particle beam only in the respiration gate, and emits the particle beam until the pattern irradiation based on the set dose from each of the scanning start pulses is completed.

To achieve the above-described object, a particle beam irradiation method according to the present invention includes the steps of: (a) generating a particle beam; (b) controlling emission of the particle beam; (c) sequentially two-dimensionally instructing a position of the particle beam so that the particle beam is scanned across the entire slice, the slice being obtained by dividing an affected region to be irradiated in an axis direction of the particle beam; (d) two-dimensionally scanning the particle beam based on an instruction signal; (e) obtaining an amount of movement of the affected region of a patient or a respiration waveform of a patient; (f) generating a respiration gate synchronized with a respiration cycle of the patient based on an obtained signal; and (g) generating a predetermined number of scanning start pulses at substantially equally spaced time intervals in the respiration gate, wherein in Step (c), the entire slice is instructed to be scanned by pattern irradiation based on a set dose from each of the scanning start pulses so that a scan of the same slice is repeated the predetermined number of times, and in Step (b), emission of the particle beam is permitted only in the respiration gate, and the particle beam is emitted until the pattern irradiation based on the set dose from each of the scanning start pulses is completed.

To achieve the above-described object, another particle beam irradiation method according to the present invention includes the steps of: (a) generating a particle beam; (b) controlling emission of the particle beam; (c) sequentially two-dimensionally indicating a position of the particle beam so that the particle beam is scanned across the entire slice, the slice being obtained by dividing an affected region to be irradiated in an axis direction of the particle beam; (d) two-dimensionally scanning the particle beam based on an indicated signal; (e) obtaining an amount of movement of the affected region by a respiration waveform or respiration of a patient; (f) generating a respiration gate synchronized with a respiration cycle of the patient based on an obtained signal; and (g) dividing a width of the respiration gate into four or more time periods, wherein in Step (b), beam emission is sequentially started in the respiration gate in synchronization with each start time of the periods divided in Step (g).

The particle beam irradiation apparatus and the particle beam irradiation method according to the present invention described above use a respiration synchronized irradiation method to eliminate the need for changing beam intensity for each slice to achieve high dose setting accuracy and a reduced therapy time, and can achieve high uniformity of dose distribution even if a respiration waveform changes during therapy irradiation.

BRIEF DESCRIPTION OF THE DRAWINGS

FIGS. 4A to 4C show a timing relationship between a respiration gate and the beam emission;

FIGS. 5A to 5G are timing charts showing basic process timing of the conventional respiration synchronized irradiation method;

FIGS. 6A to 6E show the conventional respiration synchronized irradiation method and a basic operation concept;

FIGS. 8A to 8E show a basic operation concept of the particle beam irradiation apparatus according to the first embodiment of the present invention;

FIGS. 9A to 9K are first specific operation timing charts of the particle beam irradiation apparatus according to the first embodiment;

FIGS. 10A to 10D illustrate an example of a generation method of a scanning start pulse;

FIGS. 11A to 11L are second specific operation timing charts of the particle beam irradiation apparatus according to the first embodiment;

FIGS. 13A to 13H are specific operation timing charts of a particle beam irradiation apparatus according to the second embodiment.

BEST MODE FOR CARRYING OUT THE INVENTION

Embodiments of a particle beam irradiation apparatus and a particle beam irradiation method according to the present invention will be described with reference to the accompanying drawings.

First Embodiment

Figure 7:
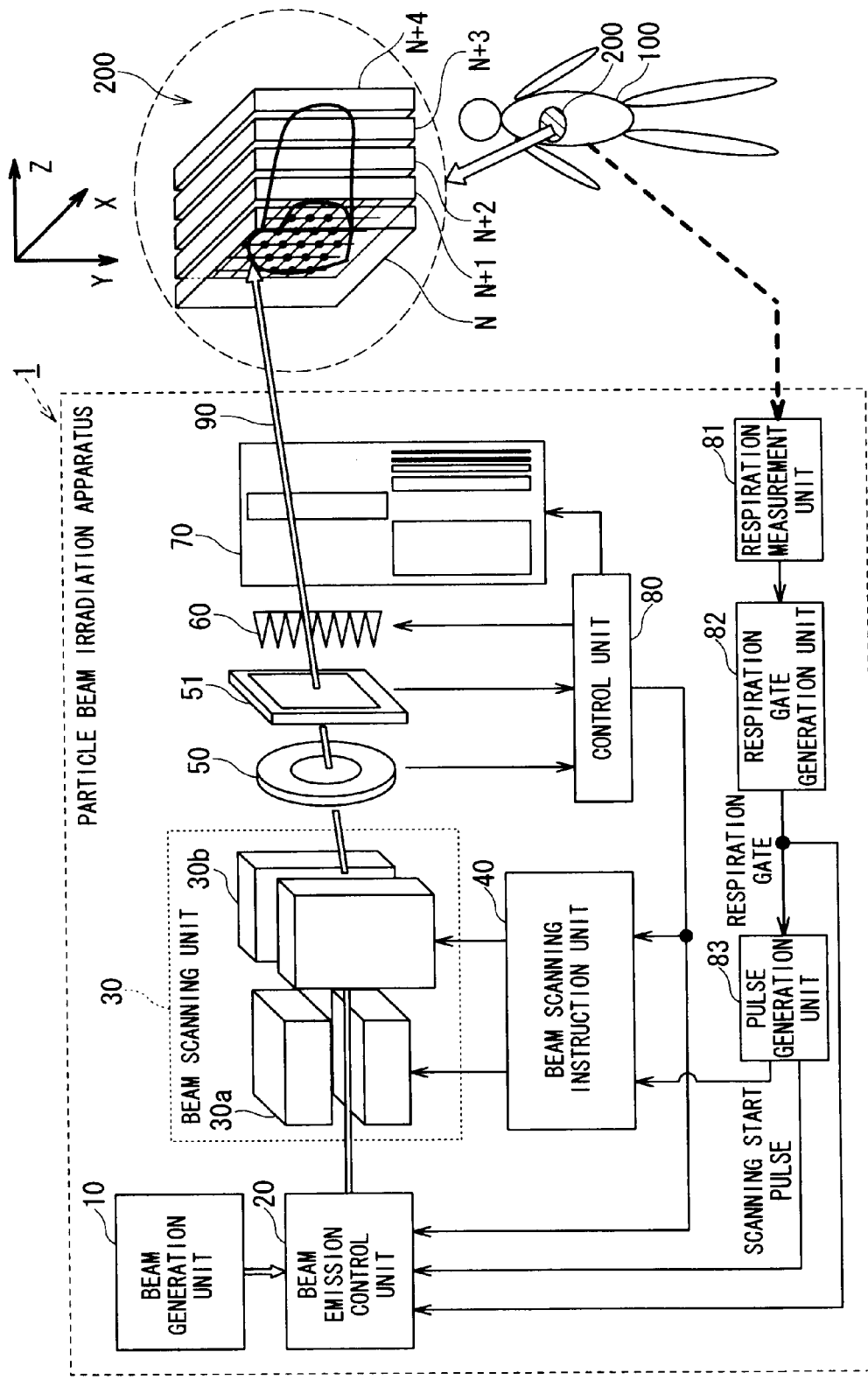
FIG. 7 shows an exemplary configuration of a particle beam irradiation apparatus according to a first embodiment of the present invention.

FIG. 7 shows an exemplary configuration of a particle beam irradiation apparatus 1 according to this embodiment. The particle beam irradiation apparatus 1 according to the first embodiment of the present invention can ensure a desired dose for every slice with the same beam intensity even if slices have different slice areas (that is, different numbers of lattice points in the slices), and does not require adjustment of the beam intensity for each slice.

Figure 1:
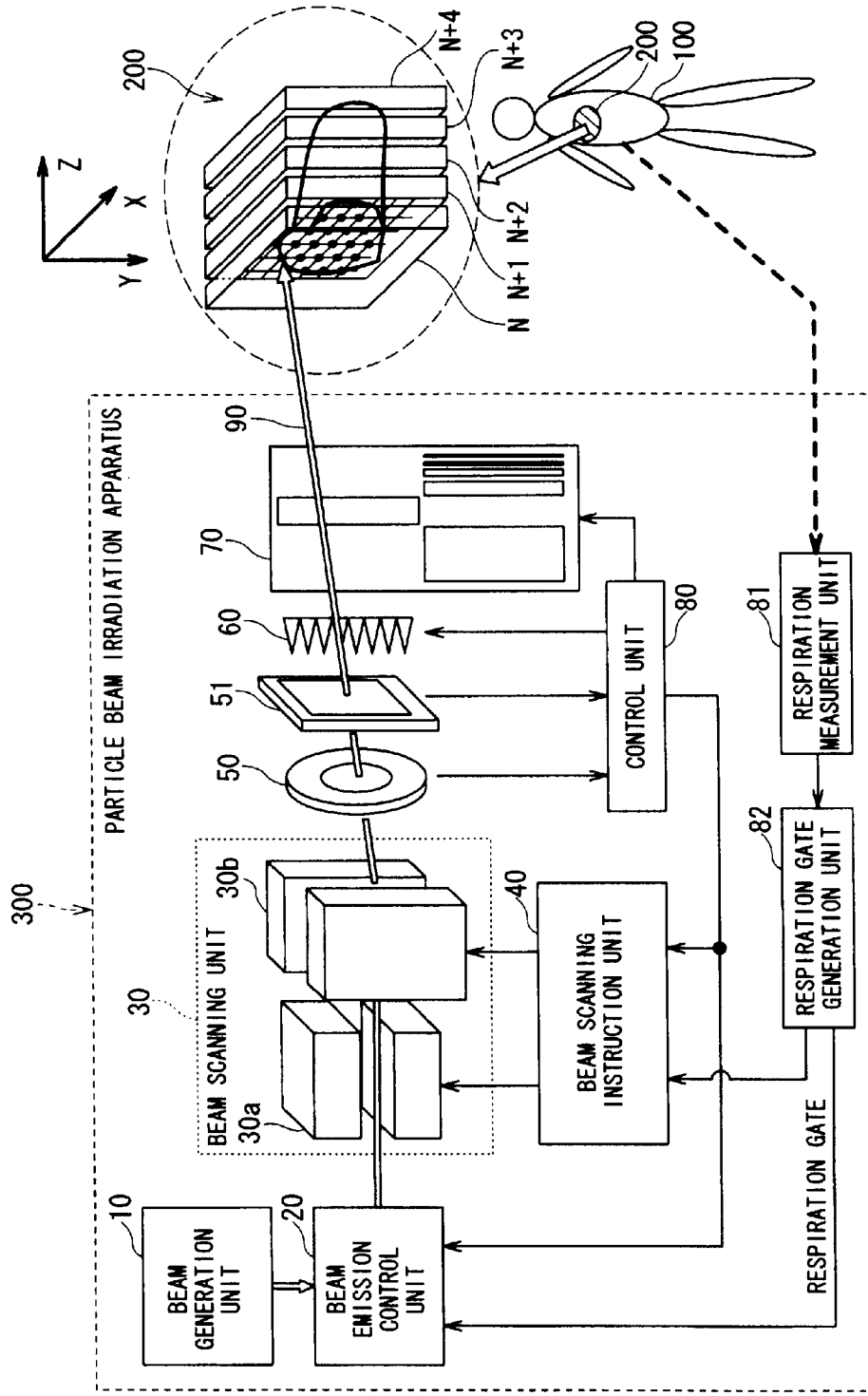
FIG. 1 shows an exemplary configuration of a conventional particle beam irradiation apparatus using a respiration synchronized irradiation method.
Figure 2:
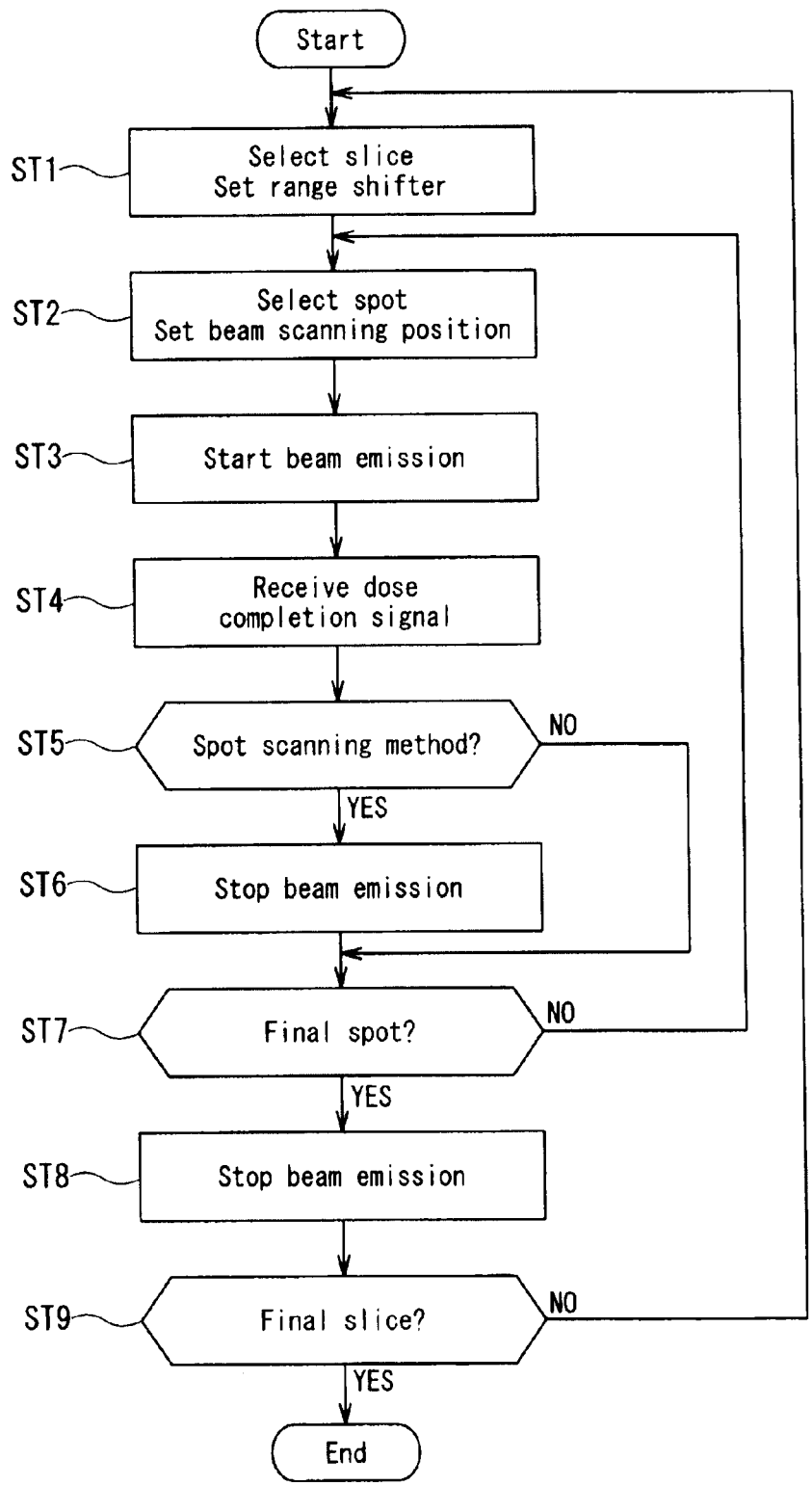
FIG. 2 is a flowchart showing a process example of conventional beam scanning and beam emission.

The particle beam irradiation apparatus 1 according to this embodiment shown in FIG. 7 is different from a conventional particle beam irradiation apparatus 300 (see FIG. 1) in including a pulse generation unit 83.

The pulse generation unit 83 generates a predetermined number of (the number of repeated scans of the same slice) scanning start pulses at substantially equally spaced time intervals in a respiration gate. The scanning start pulse is a timing pulse for determining start timing of each of the repeated scans.

FIGS. 8A to 8E show an operation concept of the particle beam irradiation apparatus 1 according to this embodiment.

The particle beam irradiation apparatus 1 according to this embodiment does not change the beam intensity depending on the slice area (that is, the number of lattice points in the slice), but performs irradiation by pattern irradiation based on a set dose previously determined by therapy planning. The set dose is ensured without changing the beam intensity, and as a result, a slice scanning time T changes depending on the area of an affected region in the slice. The slice scanning time T is a scanning time for one of the repeated scans. The slice scanning time T is determined by the sum total of irradiation times for the lattice points (including a movement time between the lattice points). FIGS. 8A to 8E show an example of performing four repeated scans of each of three slices: a slice N, a slice N+1, and a slice N+2 having increasing areas in order. The slice scanning times are $T_N<T_{N+1}<T_{N+2}$ substantially in proportion to the slice areas. Thus, as shown in FIG. 8E, irradiation with the same dose can be performed for the slices having different areas without changing the beam intensity P.

Next, more specific operation of the respiration synchronized irradiation method of the particle beam irradiation apparatus 1 according to this embodiment will be described using timing charts in FIGS. 9A to 9K. In the example described below, four repeated scans are performed for the same slice.

FIGS. 9A to 9K illustrate a case where the slice scanning time is relatively short, and four repeated scans are completed in one respiration gate such as a case where the size of the affected region is small or a low dose is required.

FIG. 9A shows a respiration waveform, and FIG. 9B shows a respiration gate (A) generated by applying an appropriate threshold to the respiration waveform. The respiration waveform is output from a respiration measurement unit 81, and the respiration gate (A) is generated by a respiration gate generation unit 82.

A pulse generation unit 83 divides a respiration gate width Gw by the number m of repeated scans to obtain an interval Gw/m between start timings of the repeated scans, and generates a timing pulse generated at the interval Gw/m, that is, a scanning start pulse (B).

FIGS. 10A to 10D show an example of a specific generation method of the scanning start pulse (B). A first scanning start pulse (1) is generated with a slight delay time t1 (margin time) from a leading edge of the respiration gate (A). Then, a second scanning start pulse (2) is generated after a t2 (t2=Gw/m) delay from a leading edge of the first scanning start pulse (1). Third and fourth scanning start pulse (3) and (4) are thereafter generated in the same manner.

The four pulses are synthesized by, for example, OR logic to generate a scanning start pulse (B) as shown in FIG. 10D.

In therapy irradiation, a range shifter 70 is first set so that a particle beam range matches a next slice position (see FIG. 9G). The control unit 80 recognizes completion of setting of the range shifter, and then generates a device ready signal (E) (see FIG. 9H).

When one scanning start pulse (B) is generated at this time, a first slice scan is started. The slice scan is actually started by an irradiation start pulse (see FIG. 9I), and the irradiation start pulse is generated by the scanning start pulse (B) in a state of the device ready (E) and not in a state of irradiation start prohibition (C) (see FIG. 9F). The irradiation start prohibition (C) is a signal for prohibiting start of a next slice scan after one slice scan is started and before the slice scan is finished. In the state of the irradiation start prohibition (C), the irradiation start pulse is not generated even if the scanning start pulse (B) is generated.

Simultaneously with the start of the first slice scan, a beam emission gate (see FIG. 9E) is opened to perform beam emission to the corresponding slice (see FIG. 9J). Thereafter, a position of the particle beam is moved every time a dose completion signal is received at each lattice point in the slice to sequentially scan the slice surface.

In a spot scanning method, the beam emission is stopped during movement between the lattice points, while in a raster scanning method, the beam emission is not stopped even during movement between the lattice points. When irradiation is performed up to a final lattice point (final spot), final spot dose completion (see FIG. 9D) is output, the beam emission gate is turned off, and then the irradiation start prohibition (c) is reset. Then, the first slice scan is finished.

When the size of the affected region is small or a low dose is required, the slice scanning time (time corresponding to the width of the beam emission gate in FIG. 9E) is short, and for example, as illustrated in FIGS. 9A to 9K, the slice scanning time is shorter than the interval between the scanning start pulses (B).

In this case, the first slice scan has been already finished and the irradiation start prohibition (c) has been reset at the time when a second scanning start pulse (B) is generated, and thus a second slice scan is started at generation timing of the second scanning start pulse (B).

Third and fourth slice scans are thereafter performed in the same manner, and four repeated scans of the same slice are automatically performed.

When the four repeated scans are finished, the device ready (E) signal is once reset, and setting of the range shifter for changing to a next slice is performed. When the setting of the range shifter is finished, the device ready state is set again so that repeated scans of the next slice can be performed.

The conventional respiration synchronized irradiation method previously determines a respiration gate width from a previously obtained respiration waveform, and determines timing specifications or beam intensity of the slice scan from the respiration gate width in the stage of therapy planning.

In contrast, the particle beam irradiation apparatus 1 according to this embodiment obtains a respiration waveform of a patient during therapy, and can update a respiration gate width Gw during therapy.

Specifically, a preferable method is obtaining a plurality of latest respiration waveforms so as not to respond to a sudden respiration change, and sequentially generating respiration gates by, for example, a moving average process for updating. It may be conceivable that a threshold is applied to an average respiration waveform of a plurality of respiration waveforms to generate a respiration gate, or a threshold is applied to each of a plurality of respiration waveforms to generate a plurality of respiration gates, and generate an average respiration gate of the plurality of respiration gates.

An interval Gw/m between the scanning start pulses (B) is calculated from the gate width Gw of the respiration gate thus updated to generate a pulse train of the scanning start pulses (B).

Based on the newly generated pulse train of the scanning start pulses (B), repeated scans of the next slice are performed as in the above-described process. When the number of lattice points in the slice is different from that in the previous slice, a slice scanning time is different as illustrated in FIGS. 9A to 9K.

FIGS. 9A to 9K show the case where the one slice scanning time T is shorter than the interval Gw/m between the scanning start pulses. Next, a case where the slice scanning time T is longer than the interval Gw/m between the scanning start pulses will be described with reference to FIGS. 11A to 11L. In this case, m repeated scans are performed over a plurality of respiration gates, and in this embodiment, start timings of the repeated scans are uniformly dispersed in the respiration gate without being concentrated at one particular spot of the respiration waveform.

In the example in FIGS. 11A to 11L, a first slice scan is not finished in one respiration gate, but continues to a finish time of a scanning start pulse (2) (second scanning start pulse (B)) of a next respiration gate. Thus, an irradiation start prohibition (C) signal also continues to the finish time of the scanning start pulse (2), and a new slice scan is not started during this period. In this case, start timing of a next slice scan is a scanning start pulse (3) (third scanning start pulse (B)), and the second slice scan is started at this timing.

In the repeated scans of the same slice, to avoid overlapping use of a scanning start pulse in the same phase (the same start timing in the respiration gate), output of the scanning start pulse once used as slice scan start timing of the same slice is set to off.

In the example in FIGS. 11A to 11L, the scanning start pulse (1) is used as the start timing of the first slice scan, and thus output of the scanning start pulse (1) is set to off immediately after the start of the first slice scan. In the second slice scan, the scanning start pulse (3) is used, and thus output of the scanning start pulse (3) is set to off immediately after the start of the second slice scan.

Thus, the next third slice scan is started at timing of the remaining scanning start pulse (2) or scanning start pulse (4). In the example in FIGS. 11A to 11L, the third slice scan is started at the timing of the scanning start pulse (4). As a result, the final fourth slice scan is started at the scanning start pulse (2).

As such, with the particle beam irradiation apparatus 1 according to this embodiment, the different numbers of lattice points depending on the slices are adjusted by eventually changing the slice scanning time. Even with different doses depending on the slices, the doses can be changed by changing the slice scanning time without changing the beam intensity. Thus, there is no need for changing and adjusting the beam intensity for each slice, thereby solving various problems due to changing the beam intensity.

When the size of the affected region is large or a high dose is required, it is supposed that a total value of m slice scanning times or one slice scanning time exceeds one respiration gate width. Even such a case can be addressed without changing a configuration of hardware or software as shown in FIGS. 11A to 11L.

Even when the scans are performed over the plurality of respiration gates, the start timings in each slice scan are uniformly dispersed in the respiration gate. This can avoid a situation where the particle beam is concentrated at a particular position in the affected region or a situation where there is a region that is completely not irradiated with the particle beam, even if the position of the affected region is slightly changed in the respiration gate.

Also, the latest respiration waveform is used in irradiation of different slices, thereby allowing stable irradiation with uniform dose distribution even if the respiration waveform of the patient changes with time.

As is apparent from FIGS. 11A to 11L, the slice scan is started using a scanning start pulse immediately after completion of a previous slice scan. This reduces a waiting time and thus reduces a therapy time as compared with when irradiation is performed in order of pulse trains of the scanning start pulses.

Randomness of the irradiated dose due to the movement of the affected region is reduced statistically by $1/\sqrt{m}$ for the number m of repeated irradiations. Specifically, the number m of repeated irradiations m for reducing the randomness to half is m=4. Thus, the number of repeated irradiations is preferable at least m≧4.

Second Embodiment

Figure 3:
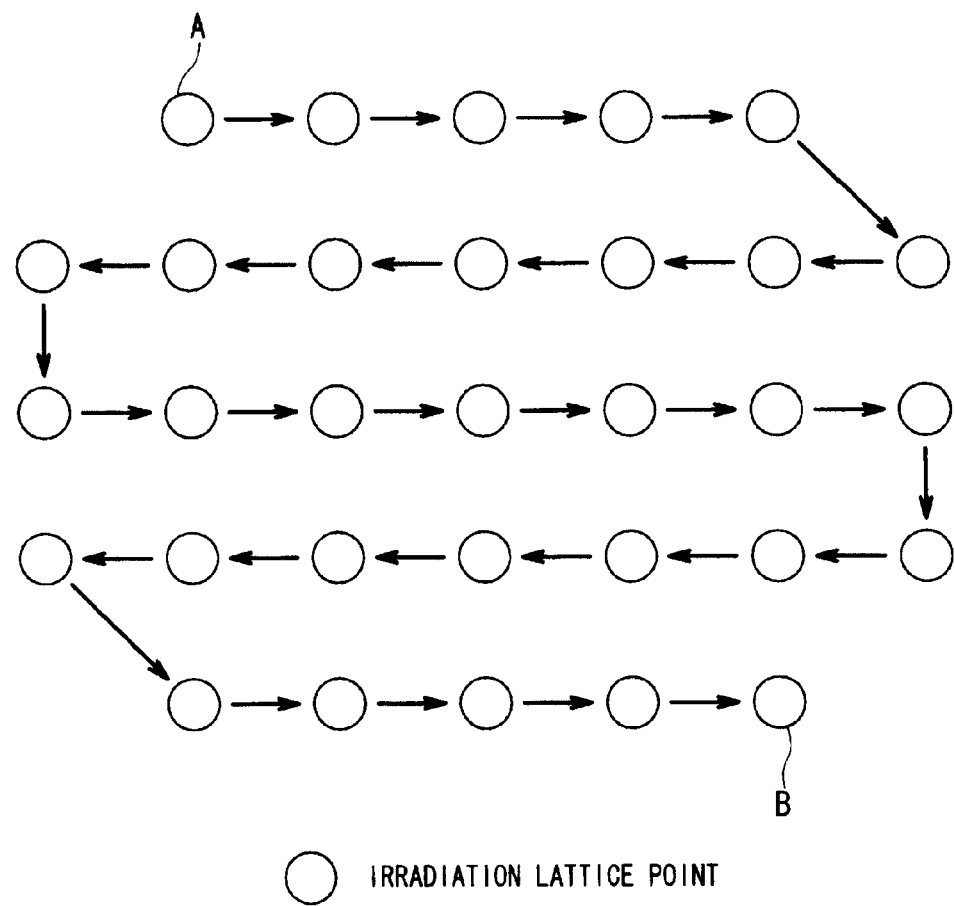
FIG. 3 illustrates a concept of the conventional beam scanning.

In the embodiment described above, a scanning direction in the slice is one direction as shown in FIG. 3.

Figure 12:
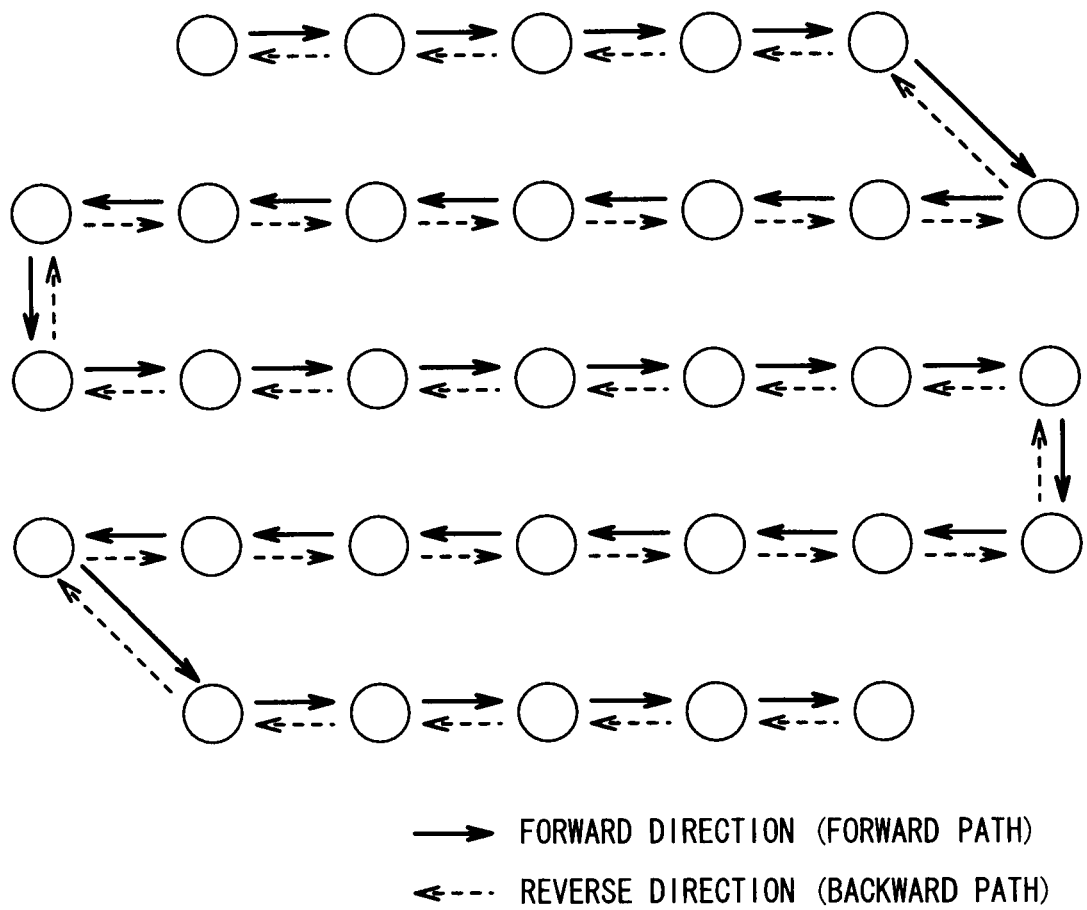
FIG. 12 shows an example of a reciprocating scanning method of a particle beam irradiation apparatus according to a second embodiment.

In a second embodiment, as shown in FIG. 12, a scanning method is used of following a path pattern on a slice in a forward direction (forward path) and then following the same path pattern in a reverse direction (backward path). A hardware configuration is the same as in the first embodiment shown in FIG. 7.

FIGS. 13A to 13H are timing charts showing operation of a particle beam irradiation apparatus 1 according to the second embodiment.

First, a scanning start pulse (for forward path) like the scanning start pulse (B) in the first embodiment is generated. This pulse train is for the forward path. This timing is used to start a slice scan of a first forward path.

In the example shown in FIGS. 13A to 13H, a slice scanning time of the forward path is set to about twice an interval Gw/m or less between the scanning start pulses (for forward path).

When a slice scan of the first forward path is completed, a slice scan of the backward path reversely following the path pattern is started, and the start timing is determined by a second scanning start pulse (for backward path). The second scanning start pulse (for backward path) is set with a certain delay time from a time of finish of the slice scan of the first forward path. The delay time is provided to provide a margin so that the slice scan of the backward path can be normally started even if the slice irradiation time of the forward path slightly changes.

Also, the second scanning start pulse (for backward path) is generated separately from the scanning start pulse (for forward path) so that the slice scan of the backward path can be started immediately after the slice scan of the forward path is finished (including the above-described delay time).

When the slice scans of the first forward and backward paths are finished, slice scans of second forward and backward paths are started. This is repeated m times to complete repeated scans of the same slice. After the repeated scans of one slice are finished, scans of a next slice are performed, and this is repeated until the entire affected region is irradiated with the particle beam.

Another Embodiment

The first and second embodiments described above relate to the respiration synchronized irradiation method in the three-dimensional scanning irradiation method. In these embodiments, a pencil-like particle beam having a small diameter is used.

However, another embodiment according to the present invention is also effective in, for example, a three-dimensional expanded beam irradiation method of performing three-dimensional irradiation by switching an in-body range using a range adjustment device in an expanded beam irradiation method (see Non-patent Document 2). In this embodiment, one slice scan in the first embodiment is replaced by irradiation of an expanded beam. Expanded beam irradiation for the same slice is repeatedly performed according to a pulse train of scanning start pulses (B), thereby allowing stable irradiation with uniform irradiation dose distribution.

In other irradiation methods, for example, in a case of performing therapy irradiation of an affected region including only one slice, the above-described repeated scanning technique is effective.

As described above, with the particle beam irradiation apparatus 1 and the particle beam irradiation method according to the embodiments, repeated irradiation can be performed at the dispersed timings in the respiration gate without adjusting beam intensity during therapy irradiation. This can reduce a therapy time, and allows irradiation with a beam having stable properties. Further, for example, even if a respiration waveform of the patient changes during therapy, synchronized irradiation is performed based on the latest respiration waveform, thereby allowing irradiation at stable irradiation timings.

The present invention is not limited to the above-described embodiments, but can be embodied with components modified without departing from the gist of the invention in implementation. Various embodiments of the invention may be formed by combinations of the plurality of components disclosed in the embodiments. For example, some components may be deleted from all the components disclosed in the embodiments. Further, the components over the different embodiments may be combined.

The invention claimed is:
1. A particle beam irradiation apparatus comprising:
a beam generation unit that generates a particle beam;
a beam emission control unit that controls emission of the particle beam;
a beam scanning instruction unit that sequentially two-dimensionally instructs a position of the particle beam so that the particle beam is scanned across an entire slice, the slice being obtained by dividing an affected region to be irradiated in an axis direction of the particle beam;
a beam scanning unit that two-dimensionally scans the particle beam based on an instruction signal from the beam scanning instruction unit;
a respiration measurement unit that obtains an amount of movement of the affected region of a patient or a respiration waveform of a patient;
a respiration gate generation unit that generates a respiration gate synchronized with a respiration cycle of the patient based on a signal output from the respiration measurement unit; and
a pulse generation unit that generates a predetermined number of scanning start pulses at substantially equally spaced time intervals in the respiration gate, the predetermined number of the scanning start pulses corresponding to a predetermined number of scans repeated in a same slice, and each of the time intervals being determined by dividing a width of the respiration gate by the number of the scans repeated in the respiration gate so that the number of the scans in each respiration gate is maintained between different respiration cycles, wherein, the beam scanning instruction unit instructs to scan the entire slice by pattern irradiation based on a set dose from each of the scanning start pulses so that a scan of the same slice is repeated the predetermined number of times, and the beam emission control unit permits emission of the particle beam only in the respiration gate, and emits the particle beam from each of the scanning start pulses until the pattern irradiation based on the set dose is completed.

2. The particle beam irradiation apparatus according to claim 1, wherein the pattern irradiation based on the set dose is set for a slice to be irradiated, and beam intensity of the particle beam is constant even for a different slice to be irradiated.

3. The particle beam irradiation apparatus according to claim 1, wherein the predetermined number of scans of the same slice can be performed over a plurality of respiration gates, and when the respiration gate is finished before completion of the pattern irradiation based on the set dose, a scan of the slice and emission of the particle beam are stopped, and the stopped scan and emission are restarted from a start point of a next respiration gate.

4. The particle beam irradiation apparatus according to claim 1, wherein the predetermined number of scans of the same slice can be performed over a plurality of respiration gates, and start timing of each scan and each emission for the same slice is determined by a pulse that is selected from the predetermined number of the scanning start pulses so that each selected pulse has a different starting timing in each of the respiration gates.

5. The particle beam irradiation apparatus according to claim 1, wherein a forward path and a backward path in a path pattern that covers the entire slice are scanned, the pulse generation unit further generates a predetermined number of second scanning start pulses for the backward path in the respiration gate at substantially equally spaced time intervals after the scan of the forward path is completed, the beam scanning instruction unit instructs the position of the particle beam so that the particle beam is scanned across the entire slice by pattern irradiation based on a set dose from each of the scanning start pulses or each of the second scanning start pulses so that the scans of the forward path and the backward path of the same slice are repeated the predetermined number of times respectively, the beam scanning unit scans the particle beam based on a instruction from the beam scanning instruction unit, and the beam emission control unit permits emission of the particle beam only in the respiration gate and emits the particle beam from each of the scanning start pulses or each of the second scanning start pulses until the pattern irradiation based on the set dose is completed.

6. The particle beam irradiation apparatus according to claim 1, wherein the respiration gate is updated based on a signal output from the respiration measurement unit.

7. The particle beam irradiation apparatus according to claim 6, wherein a gate width of the respiration gate is determined by an average waveform obtained from a plurality of respiration waveforms immediately before an update and a predetermined threshold, or determined by an average value of a plurality of gate widths obtained from the plurality of respiration waveforms immediately before the update and the predetermined threshold.

8. A particle beam irradiation method comprising the steps of:

(a) generating a particle beam;

(b) controlling emission of the particle beam;

(c) sequentially two-dimensionally instructing a position of the particle beam so that the particle beam is scanned across an entire slice, the slice being obtained by dividing an affected region to be irradiated in an axis direction of the particle beam;

(d) two-dimensionally scanning the particle beam based on an instruction signal;

(e) obtaining an amount of movement of the affected region of a patient or a respiration waveform of a patient;

(f) generating a respiration gate synchronized with a respiration cycle of the patient based on an obtained signal; and (g) generating a predetermined number of scanning start pulses at substantially equally spaced time intervals in the respiration gate, the predetermined number of the scanning start pulse corresponding to a predetermined number of scans repeated in a same slice, and each of the time intervals being determined by dividing a width of the respiration gate by the number of the scans repeated in the respiration gate so that the number of the scans in each respiration gate is maintained between different respiration cycles, wherein in Step (c), the entire slice is instructed to be scanned by pattern irradiation based on a set dose from each of the scanning start pulses so that a scan of the same slice is repeated the predetermined number of times, and in Step (b), emission of the particle beam is permitted only in the respiration gate, and the particle beam is emitted from each of the scanning start pulses until the pattern irradiation based on the set dose is completed.

9. The particle beam irradiation method according to claim 8, wherein the pattern irradiation based on the set dose is set for a slice to be irradiated, and beam intensity of the particle beam is constant even for a different slice to be irradiated.

10. The particle beam irradiation method according to claim 8, wherein the predetermined number of scans of the same slice can be performed over a plurality of respiration gates, and when the respiration gate is finished before completion of the pattern irradiation based on the set dose, a scan of the slice and emission of the particle beam are stopped, and the stopped scan and emission are restarted from a start point of a next respiration gate.

11. The particle beam irradiation method according to claim 8, wherein the predetermined number of scans of the same slice can be performed over a plurality of respiration gates, and start timing of each scan and each emission for the same slice is determined by a pulse that is selected from the predetermined number of the scanning start pulses so that each selected pulse has a different starting timing in each of the respiration gates.

12. The particle beam irradiation method according to claim 8, wherein a forward path and a backward path in a path pattern that covers the entire slice are scanned, in the Step (g), a predetermined number of second scanning start pulses for the backward path are further generated in the respiration gate at substantially equally spaced time intervals after the scan of the forward path is completed, in the Step (c), the entire slice is scanned by pattern irradiation based on a set dose from each of the scanning start pulses or each of the second scanning start pulses so that the scans of the forward path and the backward path of the same slice are repeated the predetermined number of times respectively, and in the Step (b), emission of the particle beam is permitted only in the respiration gate and the particle beam is emitted from each of the scanning start pulses or each of the second scanning start pulses until the pattern irradiation based on the set dose is completed.

13. The particle beam irradiation method according to claim 8, wherein the respiration gate is updated based on a signal output from a respiration measurement unit.

14. The particle beam irradiation method according to claim 13, wherein a gate width of the respiration gate is determined by an average waveform obtained from a plurality of respiration waveforms immediately before an update and a predetermined threshold, or determined by an average value of a plurality of gate widths obtained from the plurality of respiration waveforms immediately before the update and the predetermined threshold.

15. A particle beam irradiation method comprising the steps of:

(a) generating a particle beam;
(b) controlling emission of the particle beam;
(c) sequentially two-dimensionally instructing a position of the particle beam so that the particle beam is scanned across an entire slice, the slice being obtained by dividing an affected region to be irradiated in an axis direction of the particle beam;
(d) two-dimensionally scanning the particle beam based on an instructed signal;
(e) obtaining an amount of movement of the affected region of a patient or a respiration waveform of a patient;
(f) generating a respiration gate synchronized with a respiration cycle of the patient based on an obtained signal; and
(g) dividing a width of the respiration gate into four or more time periods, wherein in Step (b), beam emission is sequentially started in the respiration gate in synchronization with each start time of the periods divided in Step (g) so that the number of the scans in each respiration gate is maintained between different respiration cycles.

* * * * *